United States Patent
Zhang et al.

(10) Patent No.: US 11,091,782 B2
(45) Date of Patent: Aug. 17, 2021

(54) ENGINEERED ZYMOMONAS FOR THE PRODUCTION OF 2,3-BUTANEDIOL

(71) Applicant: Alliance for Sustainable Energy, LLC, Golden, CO (US)

(72) Inventors: Min Zhang, Lakewood, CO (US); Yat-Chen Chou, Lakewood, CO (US); Mary Ann Franden, Centennial, CO (US); Michael E. Himmel, Littleton, CO (US)

(73) Assignee: Alliance for Sustainable Energy, LLC, Golden, CO (US)

( * ) Notice: Subject to any disclaimer, the term of this patent is extended or adjusted under 35 U.S.C. 154(b) by 0 days.

(21) Appl. No.: 16/173,910

(22) Filed: Oct. 29, 2018

(65) Prior Publication Data

US 2019/0153483 A1 May 23, 2019

Related U.S. Application Data

(60) Provisional application No. 62/578,131, filed on Oct. 27, 2017.

(51) Int. Cl.

| | |
|---|---|
| *C12P 7/18* | (2006.01) |
| *C12N 9/10* | (2006.01) |
| *C12N 9/04* | (2006.01) |
| *C12N 9/88* | (2006.01) |

(52) U.S. Cl.
CPC ............. *C12P 7/18* (2013.01); *C12N 9/0006* (2013.01); *C12N 9/1022* (2013.01); *C12N 9/88* (2013.01); *C12Y 101/01004* (2013.01); *C12Y 202/01006* (2013.01); *C12Y 401/01001* (2013.01); *C12Y 401/01005* (2013.01)

(58) Field of Classification Search
None
See application file for complete search history.

(56) References Cited

U.S. PATENT DOCUMENTS

| | | | | |
|---|---|---|---|---|
| 7,354,755 | B2 * | 4/2008 | Zhang | C12N 9/1022 435/252.3 |
| 7,998,722 | B2 * | 8/2011 | Viitanen | C12N 9/0008 435/161 |
| 8,465,961 | B2 * | 6/2013 | Caimi | C12N 1/20 435/252.1 |
| 2009/0162910 | A1 * | 6/2009 | Seo | C12N 9/0006 435/145 |

OTHER PUBLICATIONS

Yang et al. Biotechnol Biofuels. Sep. 2, 2016;9(1):189 (Year: 2016).*
Chica et al. Curr Opin Biotechnol. Aug. 16, 2005(4):378-84. (Year: 2005).*
Singh et al. Curr Protein Pept Sci. 2017, 18, 1-11 (Year: 2017).*
Kizeretal. Appl Environ Microbiol. May 2008;74(10):3229-41. (Year: 2008).*
Prather et al. Curr Opin Biotechnol. Oct. 2008;19(5):468-74. (Year: 2008).*
Rao et al. Appl Microbiol Biotechnol. Mar. 2012;93(5):2147-59. (Year: 2012).*
Yanase et al. Appl Microbiol Biotechnol. Jun. 2012;94(6):1667-78. (Year: 2012).*
Chen et al., "A Highly Efficient Dilute Alkali Deacetylation and Mechanical (disc) Refining Process for the Conversion of Renewable Biomass to Lower Cost Sugars", Biotechnology for Biofuels, 2014, vol. 7, No. 98, pp. 1-11.
Zhao, "Genetic Characterization and Manipulation of Strains of Zymomonas mobilis for Ethanol and Higher Value Products", Master Research in Biotechnology, School of Biotechnology and Biomolecular Sciences, University of South Wales, Sydney, Australia, Mar. 2011, pp. 1-114.

* cited by examiner

*Primary Examiner* — Christian L Fronda
(74) *Attorney, Agent, or Firm* — Sam J. Barkley

(57) ABSTRACT

Non-naturally occurring *Zymomonas* strains useful for the production of 2,3-butanediol are provided.

5 Claims, 12 Drawing Sheets

Specification includes a Sequence Listing.

WT pdc band: 4.0 kb
pdc KO (CmloxP) band: 3.4 kb

ENGINEERED ZYMOMONAS FOR THE PRODUCTION OF 2,3-BUTANEDIOL

CROSS-REFERENCE TO RELATED APPLICATIONS

This application claims priority under 35 U.S.C. § 119 to U.S. Provisional Patent Application No. 62/578,131 filed on 27 Oct. 2017, the contents of which are hereby incorporated in their entirety.

CONTRACTUAL ORIGIN

The United States Government has rights in this invention under Contract No. DE-AC36-08GO28308 between the United States Department of Energy and the Alliance for Sustainable Energy, LLC., the Manager and Operator of the National Renewable Energy Laboratory.

SEQUENCE LISTING

The instant application contains a Sequence Listing which has been submitted via EFS-web and is hereby incorporated by reference in its entirety. The ASCII copy, created on 6 Feb. 2019, is named NREL_17-80_seq_listing_06Feb2019_ST25.txt, and is 3 kilobytes in size.

BACKGROUND

*Zymomonas mobilis* is a gram-negative, facultative anaerobic microorganism. The optimal temperature for growth of most strains of *Z. mobilis* is between 25 and 30° C., and optimal pH is about 5.0. *Z. mobilis* has the ability to rapidly and efficiently produce ethanol. Native *Z. mobilis* is only able to ferment sucrose, glucose and fructose.

SUMMARY

In an aspect, disclosed herein is a non-naturally occurring *Zymomonas* species capable of making 2,3-butanediol through using the gene products of exogenous genes. In an embodiment, the non-naturally occurring *Zymomonas* species contains the exogenous genes responsible for the production of 2,3-butanediol on an extrachromosomal plasmid. In an embodiment, the non-naturally occurring *Zymomonas* species does not contain a functional pyruvate decarboxylase gene. In another embodiment, the non-naturally occurring *Zymomonas* species does not produce ethanol. In an embodiment, the non-naturally occurring *Zymomonas* species has exogenous genes responsible for the production of 2,3-butanediol that are integrated into the chromosome of the *Zymomonas*. In another embodiment, the non-naturally occurring *Zymomonas* species does not contain a functional pyruvate decarboxylase gene. In yet another embodiment, the non-naturally occurring *Zymomonas* species has exogenous genes for the production of 2,3-butanediol that are integrated into the chromosomal endogenous pyruvate decarboxylase gene of the *Zymomonas* species. In an embodiment, the non-naturally occurring *Zymomonas* does not contain an antibiotic marker. In another embodiment, the non-naturally occurring *Zymomonas* species is capable of the production of 2,3-butanediol at about 120 g/L. In yet another embodiment, the non-naturally occurring *Zymomonas* species is capable of the production of 2,3-butanediol for at least 150 hours. In an embodiment, the non-naturally occurring *Zymomonas* species is capable of the production of 2,3-butanediol at about 2.18 g/L/h. In an embodiment, the non-naturally occurring *Zymomonas* species production of ethanol is decreased by greater than 50%, 75%, 90%, 95% or 99% in comparison to a naturally occurring *Zymomonas*. In an embodiment, the non-naturally occurring *Zymomonas* species *Zymomonas mobilis*. In another embodiment, the non-naturally occurring *Zymomonas* species has exogenous genes that encode for acetolactate synthase (ALS), acetolactate decarboxylase (ALDC), and butanediol dehydrogenase (BDH). In another embodiment, the non-naturally occurring *Zymomonas* species has exogenous genes that are operably linked to each other. In an embodiment, the non-naturally occurring *Zymomonas* species has exogenous genes that are endogenous to organisms selected from the group consisting of *Bacillus subtilis*, *Enterobacter cloacae* and *Serratia marcescens*. In another embodiment, the non-naturally occurring *Zymomonas* species uses at least one sugar selected from the group consisting of glucose and xylose as a carbon source for the production of 2,3-butanediol.

In an aspect, disclosed herein is a method for making 2,3-butanediol using a non-naturally occurring *Zymomonas* species capable of making 2,3-butanediol by using the gene products of exogenous genes.

In another aspect, a method is disclosed herein for making 2,3-butanediol using a non-naturally occurring *Zymomonas* species that uses at least one sugar selected from glucose and xylose as a carbon source for the production of 2,3-butanediol.

BRIEF DESCRIPTION OF THE DRAWINGS

FIG. 5A depicts the growth of PDC knockout BDO-producing *Z. mobilis* integrates. FIG. 5B depicts the glucose concentrations over time in growth media of PDC knockout BDO-producing *Z. mobilis* integrates. FIG. 5C depicts the BDO concentrations over time in growth media of PDC knockout BDO-producing *Z. mobilis* integrates. FIG. 5D depicts the ethanol concentrations over time in growth media of PDC knockout BDO-producing *Z. mobilis* integrates.

FIG. 7A depicts the fermentation profile of a PDC knockout BDO producing *Z. mobilis* strain in DMR corn stover hydrolysate at 20% using an air sparge technique. FIG. 7B depicts the fermentation profile of a PDC knockout BDO producing *Z. mobilis* strain in DMR corn stover hydrolysate at 20% using an air overlay technique.

FIG. 9A depicts the profiles of the concentrations of glucose, xylose, acetoin, glycerol, BDO, and the $OD_{600}$ in the hydrolysate liquor of the growth media. FIG. 9B depicts the profiles of the concentrations of glucose, xylose, acetoin, glycerol, BDO, and the $OD_{600}$ in the whole slurry (without separation of biomass solids) mixture of the growth media.

DETAILED DESCRIPTION

Figure 1:
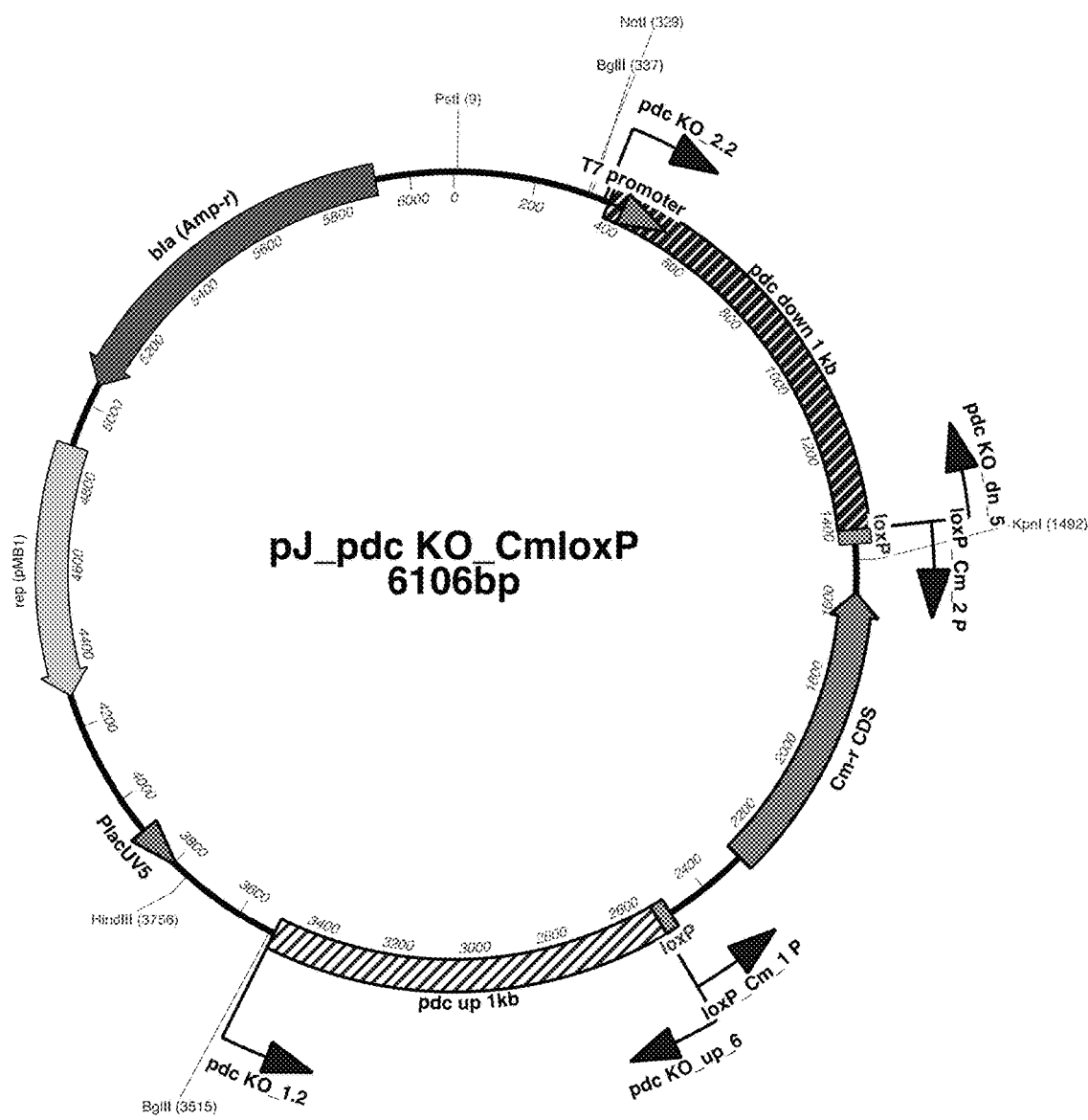
FIG. 1 depicts a pdc knockout construct in a suicidal plasmid vector.

Disclosed herein are non-naturally occurring *Zymomonas* organisms engineered for the production of 2,3-butanediol (2,3-BDO also referred to herein as BDO). In an embodiment the *Zymomonas* species is *Z. mobilis*.

In an embodiment, the pdc gene of a *Z. mobilis* strain containing a plasmid with exogenous 2,3-BDO pathway genes was knocked out. As a result, an increase in 2,3-BDO titer of greater than about 40 g/L from 10% glucose and complete elimination of ethanol production was achieved. In an embodiment, non-naturally occurring *Z. mobilis* strains disclosed herein are capable of producing 42-48 g/L of 2,3-BDO from glucose and xylose in 20% solid loading DMR hydrolysate. In another embodiment, non-naturally occurring *Z. mobilis* strains disclosed herein are capable of producing about 120 g/L of 2,3-BDO from glucose and xylose.

DMR Treatment of Corn Stover

The deacetylation and mechanical refining (DMR) process of treating corn stover consists of a mild, dilute alkaline extraction stage followed by mechanical refining to overcome the recalcitrance of the lignocellulosic biomass. Deacetylation facilitates the enzymatic hydrolysis by removing most of the acetyl groups bound to hemicellulose and partial removal of the lignin component. The following mechanical refining stage increases the surface area of biomass by mechanical fibrillation and hence greatly improves the cellulose and hemicellulose accessibility to enzymes. Furthermore, high sugar concentrations and low chemical inhibitor concentrations achieved by the DMR process allow for high titers of fermentation metabolites and products.

Engineered *Z. mobilis*

*Z. mobilis* strains were engineered to develop pathways for biological upgrading of sugars to hydrocarbons. These pathways are capable of producing intermediates amenable to separation and catalytic upgrading to hydrocarbon fuels. In an embodiment, anaerobic xylose and glucose fermenting *Z. mobilis* strains were engineered to redirect carbon from ethanol production to 2,3-BDO by taking advantage of the high specific sugar uptake rate, rapid catabolism, and high carbon yield of *Z. mobilis*. Non-naturally occurring *Z. mobilis* strains disclosed herein were engineered to efficiently use biomass derived mixed C5/C6 sugar streams commonly used for ethanol production.

2,3-BDO is much less toxic than ethanol, the product of naturally occurring *Z. mobilis*. *Z. mobilis* is capable of growth at >100 g/L 2,3-BDO. Therefore, a much high titer of *Z. mobilis* producing 2,3-BDO as either the sole or primary product can be obtained when compared to the production of ethanol.

In an embodiment, engineered 2,3-BDO-producing *Z. mobilis* strains can be used to solely produce 2,3-BDO or can be engineered to produce a mixture of 2,3-BDO and ethanol from mixed C5/C6 sugar streams derived from biomass. Both ethanol and 2,3-BDO can be further catalytically upgraded via deoxydehydration and oligomerization to hydrocarbon fuels. Alternatively, 2,3-BDO can be converted to MEK or 1,3-butadiene via a dehydration step, which can be used for polymer syntheses.

In an embodiment, engineered *Z. mobilis* strains produced 2,3-BDO by using exogenous genes encoding acetolactate synthase (ALS), acetolactate decarboxylase (ALDC), and butanediol dehydrogenase (BDH), referred to herein as "the 2,3-BDO pathway", from, but not limited to, *Bacillus subtilis, Enterobacter cloacae* and *Serratia marcescens*. In an embodiment, engineered *Z. mobilis* strains channeled pyruvate to acetolactate, then to acetoin, and then to 2,3-BDO using primarily glucose and xylose as a carbon source. The engineered 2,3-BDO pathway in *Z. mobilis* is efficient as it consists of only three enzymatic steps from pyruvate.

Disclosed herein are engineered *Z. mobilis* strains where carbon is redirected from producing ethanol to producing 2,3-BDO. In an embodiment all carbon is redirected from producing ethanol to producing 2,3-BDO. In other embodiments, a portion of carbon is redirected from producing ethanol to producing 2,3-BDO. In an embodiment the pyruvate node is altered to shift carbon flux towards production of 2,3-BDO.

Attempts at knocking out the pdc gene in native *Zymomonas* strains have been reported, but none have produced 2,3-BDO instead of ethanol. Previously, copies of both a disrupted pdc gene and a native copy of the pdc gene have been reported. These pseudo-pdc knockout *Z. mobilis* mutants produced ethanol due to the presence of native pdc gene.

Without being bound by theory, an organism containing only copies of a pdc knockout mutant might result in lethality because there might be no other sustainable pathways capable of providing a redox balance. Disclosed herein are engineered *Z. mobilis* strains showing that the presence of a BDO pathway alleviates the redox imbalance due to a pdc knockout.

In an embodiment, disclosed herein are *Z. mobilis* strains containing only disrupted (knockout) pdc genes. Knocking out the pdc gene in *Z. mobilis* strain BC21 resulted in redirecting carbon from ethanol production to 2,3-BDO production, substantially eliminating ethanol production. This lack of ethanol significantly improved product titer as well as simplifying any downstream purification processes. In an embodiment, 2,3-BDO titers of greater than 35 g/L from glucose and xylose at 35 g/L were obtained by growing engineered *Z. mobilis* strains using batch and/or fed-batch fermentations.

As disclosed herein, engineered strains were selected for growth and production parameters such as 2,3-BDO titer, production rates, and yield. In an embodiment, engineered strains were selected for improved BDO production of at least 10 g/L at 24 h. Other parameters affecting 2,3-BDO production were discovered such as promoter strength for expression, sources of pathway genes (including ALS and BDH), as well as fermentation parameters affecting 2,3-

BDO production. These experiments resulted in, for example, a Z. mobilis strain 9C-BC11 which produced 22.6 g 2,3-BDO/L from 10% glucose under low oxygen conditions obtaining 96% of the theoretical yield from glucose for the combined 2,3-BDO, acetoin, and ethanol products.

Redirecting Carbon Flow Towards 2,3-BDO Synthesis

Figure 3:
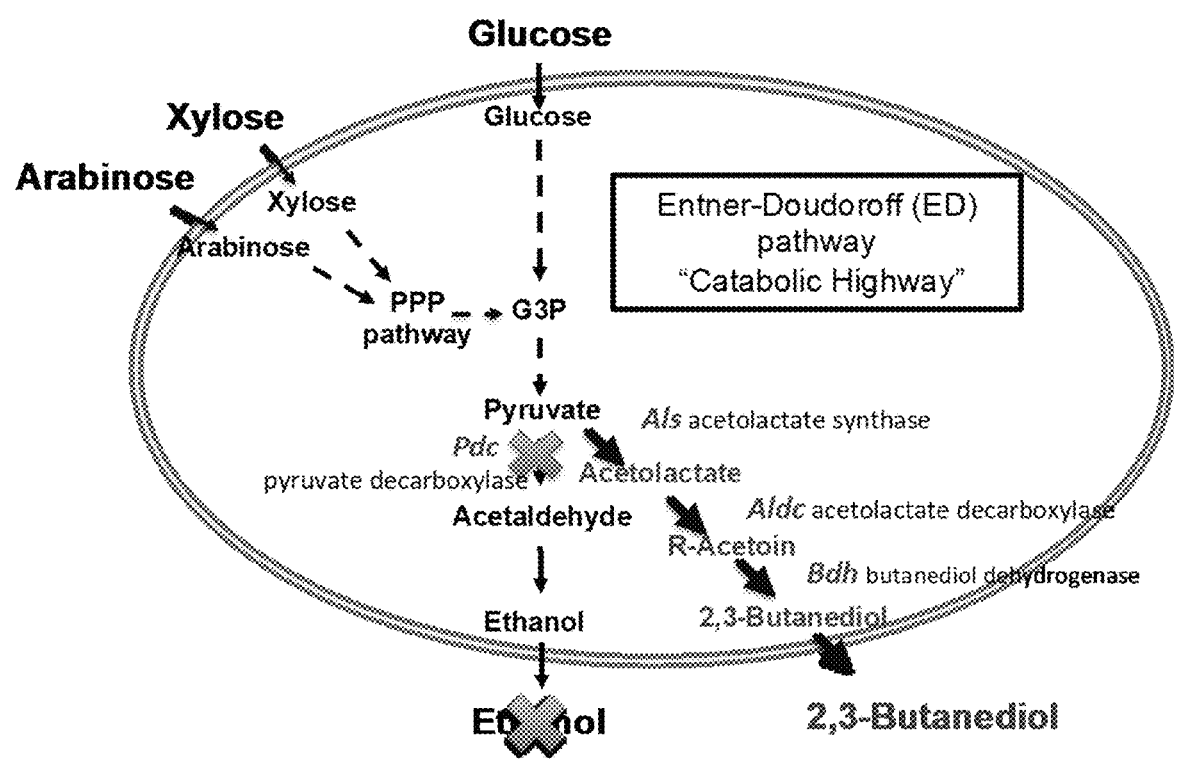
FIG. 3 is a schematic depiction of a pdc knockout strategy in a non-naturally occurring 2-3-BDO producing *Z. mobilis*.

In an embodiment, a heterologous 2,3-BDO pathway including the genes encoding acetolactate synthase (ALS), acetolactate decarboxylase (ALDC), and butanediol dehydrogenase (BDH) were introduced into Z. mobilis. In an embodiment, some engineered strains produced 2,3-BDO at 3 to 5 g/L from 8% glucose as well as producing ethanol. Experiments to determine gene expression, gene sources for ALS and BDH as well as fermentation conditions resulted in higher 2,3-BDO production of up to about 22.6 g/L 2,3-BDO from 10% glucose and had decreased ethanol production. This demonstrated that carbon can be significantly redirected from ethanol formation towards 2,3-BDO production at the pyruvate node. To further increase 2,3-BDO production, carbon flux towards ethanol was eliminated by knocking out the pdc gene, see FIG. 3.

In an embodiment, a BDO producing recombinant strain Z. mobilis BC21 was used as a host to "knock out" the pdc gene. BC21 is a derivative of Z. mobilis 9C (antibiotic resistance marker free) harboring a plasmid pBC21 (with BDO pathway genes—als, aldc and bdh).

To knock out pdc, a PCR fragment (pdcup-CmloxP-pdcdn) containing CmloxP flanked with 1 kb each of up- and downstream of pdc (FIG. 2) was used to transform BC21 (and 9C). In addition, a suicidal vector containing this fragment was used for the transformation (pJpdcKOCmloxP), see FIG. 1. Transformation (electroporation) mixtures were incubated microaerobically in the unbaffled shake flasks before plating on antibiotic containing RMG5 plates. As a comparison, additional transformation mixtures were incubated statically before plating. The plates were incubated microaerobically (plates incubated at 30° C.) or anaerobically (plates incubated at 30° C. in anaerobic jars with GasPaks) based on their respective conditions of 8 h culturing. For the BC21 transformation, incubated cultures were plated either on CmSp or Cm plates. For 9C transformation, cultures were plated only on Cm plates.

After four days of incubation, no colonies were found for BC21 transformed with PCR fragments whereas colonies were found with pJpdcKOCmloxP transformation: four colonies on a Cm plate (aerobic incubation), 17 colonies on CmSp plates (anaerobic incubation), and three colonies on a Cm plate (anaerobic). For 9C transformation, fewer colonies were obtained with PCR fragment (three colonies on Cm plates, aerobic) than with pJpdcKOCmloxP: 1280 colonies on Cm plates (anaerobic) and 71 on Cm plates (aerobic). Colonies were picked and patched onto fresh plates containing respective antibiotic(s) of which plates they were picked from and further incubated based on their respective aeration conditions of how the source plates were incubated. About 94% colonies grew up on Cm plates. Only two of the 17 colonies grew on CmSp plates from BC21 transformants. The grown colonies were patched two more times onto fresh sets of plates. Twenty-six colonies (representing aeration and antibiotics selection conditions) from the $3^{rd}$ set of plates were inoculated in 5 mL RMG5 with Cm or CmSp for genomic DNA extraction. PCR analysis of the gDNAs indicated both the wild-type PDC and the knockout PDC were present in these colonies. Without being bound by theory, it is possible that colonies were not monocultures and/or these Zymomonas cultures contained two chromosomal copies, one with wild-type and the other with pdcKO.

Serial transfers were performed for the liquid cultures of all 12 colonies (of the 26) under microaerobic condition to purify single colonies and encourage the PDC knockout selection. After 10 transfers (estimated 50 generations), cultures were streaked onto RMG5 plates with respective antibiotics for single colonies. Two colonies were picked per each of the 12 cultures (eight for BC21 transformants and four for 9C transformants) and inoculated in RMG5CmSp or RMG5Cm for overnight for gDNA extraction. The supernatants were analyzed by HPLC for BDO and ethanol. The results of the PCR of the gDNA are shown in FIG. 4.

Figure 4:
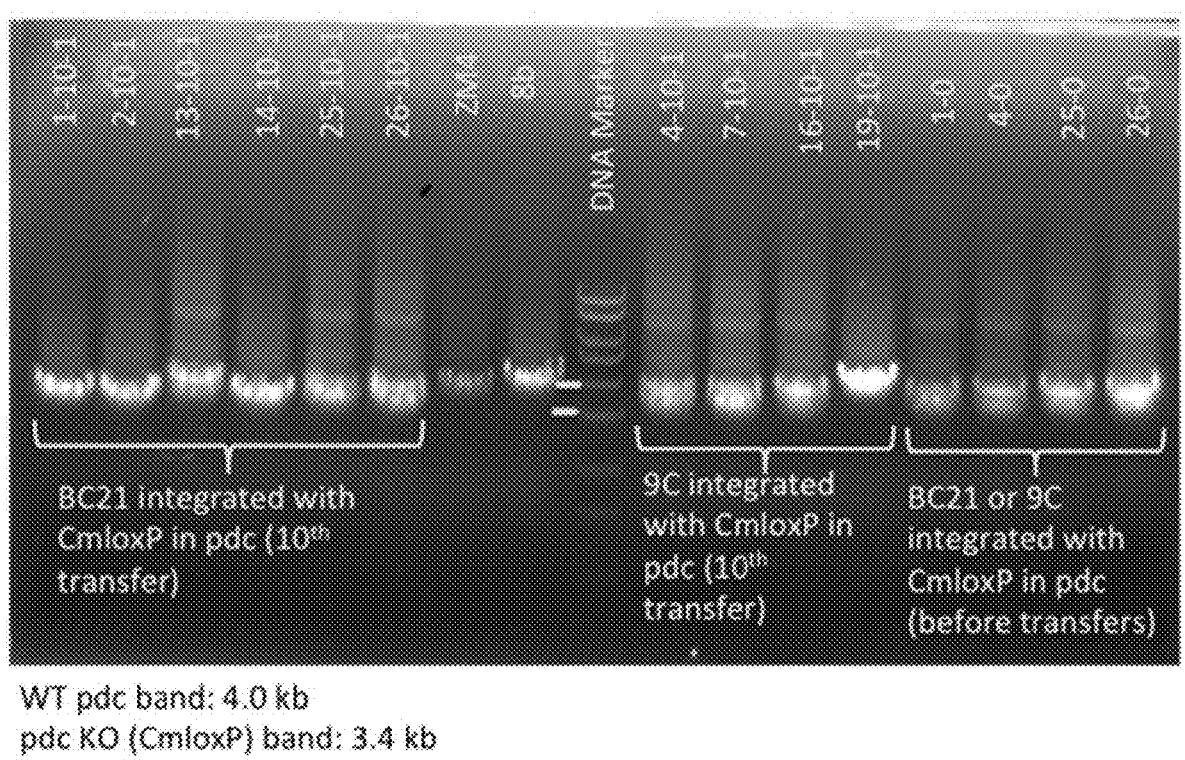
FIG. 4 is an image of a gel depicting the results of PCRs using pdcKO outside primers and gDNA as templates. The 4$^{th}$ band from the top of the DNA marker is 4 kb, the band below is 3 kb.

Based on the PCR analysis and the agarose gel depicted in FIG. 4, BC21 integrants 1, 2 and 14 after the tenth transfer (1-10-1, 2-1-1 and 14-10-1) yielded colonies with pdcKO (single PCR product corresponding to the size of CmloxP in place of the pdc in the genome). Colonies 13, 25 and 26 of BC21 integrants as well as colonies of all 9C integrants still contained PCR products (double bands) corresponding to a wild-type PDC and PDC knockout, as we previously observed.

Table 1 summarizes the results of HPLC analysis of the culture supernatants of the PDC knockout transformants/integrants after 10 serial transfers from the above-mentioned colonies grown on RMG5. It clearly shows that only the colonies with pdcKO produced high amounts of 2,3-BDO and no ethanol (the low level of ethanol of 2.67 to 2.82 g/L was from the antibiotic Cm added which was dissolved in ethanol), while all other colonies either were poor users of glucose or produced high amounts of the ethanol. Thus, PDC activity was knocked out in a non-naturally occurring 2,3-BDO producing Z. mobilis.

TABLE 1

| Medium | Colony | Glucose g/L | Acetoin g/L | BDO g/L | Ethanol g/L | BDO g/g glu | ETOH g/g glu | pdcKO out-1/-2 |
|---|---|---|---|---|---|---|---|---|
| Initial glucose 50 g/L 3-mL RMG5 in 15-mL flasks 30 C., 120 rpm PCR gDNA ||||||||
| BC21 pdcKO integrants (after 10 transfers) single colonies ||||||||
| RMG5SpCm | 1-10-1 | 19.14 | 0.20 | 13.37 | 2.82 | 0.43 | 0.09 | single 3.4 kb |
| RMG5SpCm | 2-10-1 | 20.84 | 0.21 | 12.65 | 2.76 | 0.43 | 0.09 | single 3.4 kb |
| RMG5SpCm | 13-10-1 | 41.21 | 0.58 | 0.97 | 3.26 | 0.11 | 0.37 | double 3.4/4 kb |
| RMG5SpCm | 14-10-1 | 18.57 | 0.13 | 13.44 | 2.67 | 0.43 | 0.08 | single 3.4 kb |
| RMG5SpCm | 25-10-1 | 0 | 1.91 | 7.74 | 15.97 | 0.15 | 0.32 | double 3.4/4 kb |
| RMG5SpCm | 26-10-3 | 0 | 1.80 | 4.53 | 19.03 | 0.09 | 0.38 | double 3.4/4 kb |
| 9C pdcKO integrants (after 10 transfers) ||||||||
| RMG5Cm | 4-10-1 | 17.92 | 2.60 | 0.93 | 11.99 | 0.03 | 0.37 | double 3.4/4 kb |
| RMG5Cm | 7-10-1 | 36.32 | 1.32 | 1.25 | 4.21 | 0.09 | 0.31 | double 3.4/4 kb |

TABLE 1-continued

Initial glucose 50 g/L 3-mL RMG5 in 15-mL flasks 30 C., 120 rpm PCR gDNA

| Medium | Colony | Glucose g/L | Acetoin g/L | BDO g/L | Ethanol g/L | BDO g/g glu | ETOH g/g glu | pdcKO out-1/-2 |
|---|---|---|---|---|---|---|---|---|
| RMG5Cm | 16-10-1 | 39.77 | 0.81 | 1.19 | 3.24 | 0.12 | 0.32 | double 3.4/4 kb |
| RMG5Cm | 19-10-1 | 0.41 | 3.27 | 0.67 | 20.38 | 0.01 | 0.41 | single (high) |

Figure 5:
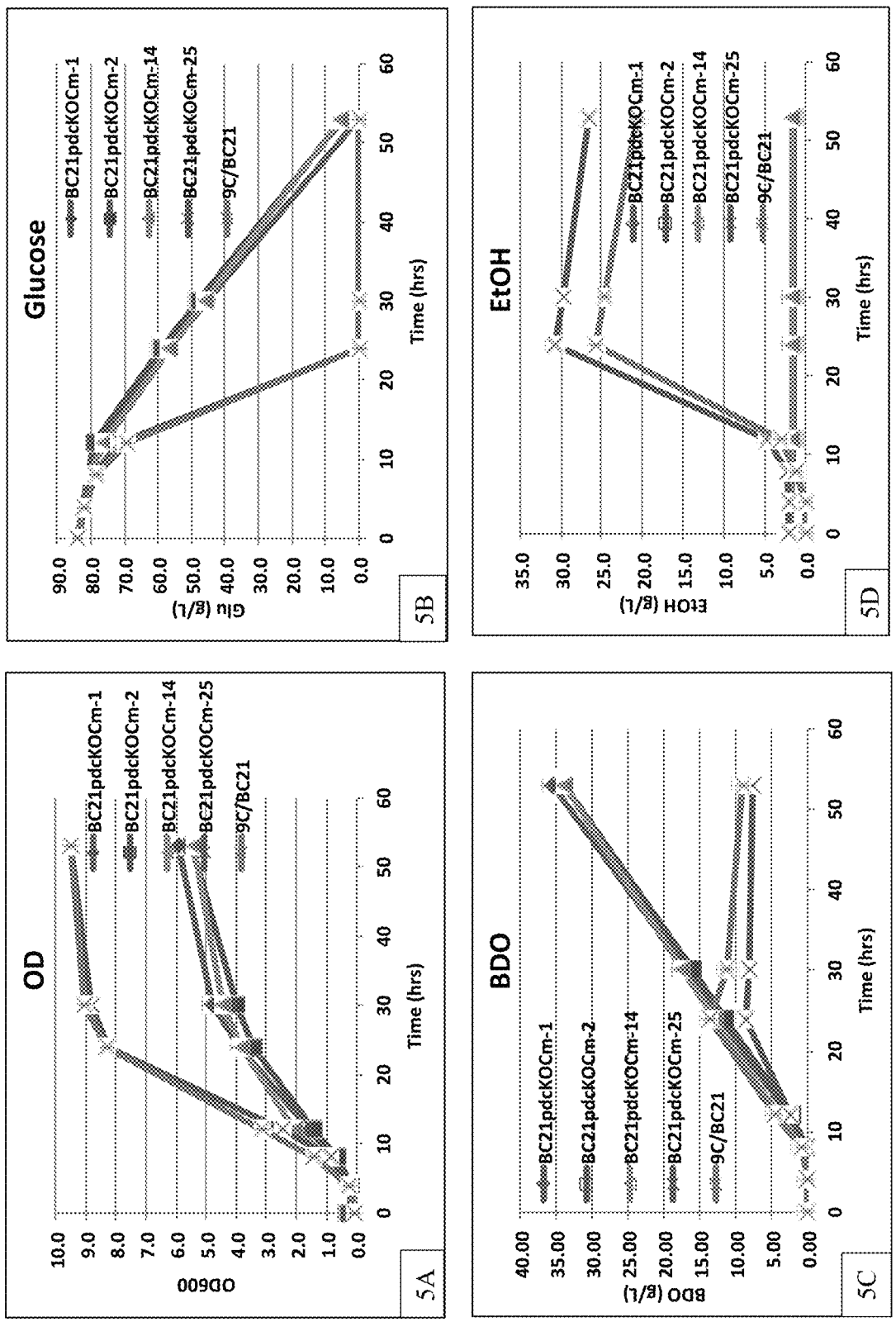
FIG. 5 depicts the fermentation profiles of PDC knockout BDO-producing *Z. mobilis* integrates.
Figure 6:
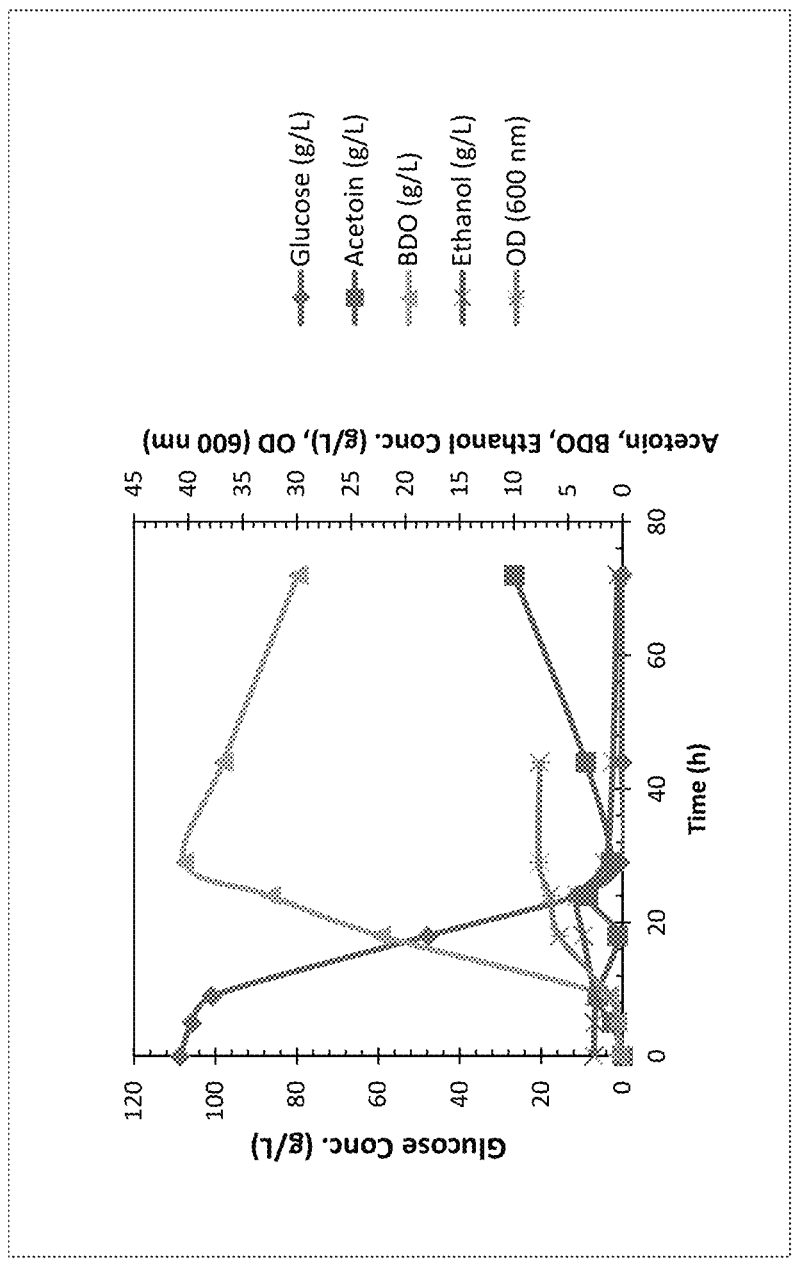
FIG. 6 depicts the fermentation profiles of a PDC knockout BDO producing *Z. mobilis* strain in RM medium containing 8% glucose.

BC21 integrants 1, 2 and 14 (with single PDC KO fragment) were selected; as well as 25 (still contains both bands of wild-type PDC and PDC knockout along with the parent strain BC21) and flask tests were conducted in RMG 8% glucose under 180 rpm shaking. The results are shown in FIG. 5. All three BC21 integrants 1, 2 and 14 produced only 2,3-BDO and no ethanol as expected, while the parent strain BC21 and the integrant 25 which contains two both wild-type PDC and PDC knockout bands produced 2,3-BDO and ethanol. All three integrants are capable of producing about 35 g/L 2,3-BDO from 8% of glucose.

Figure 7:
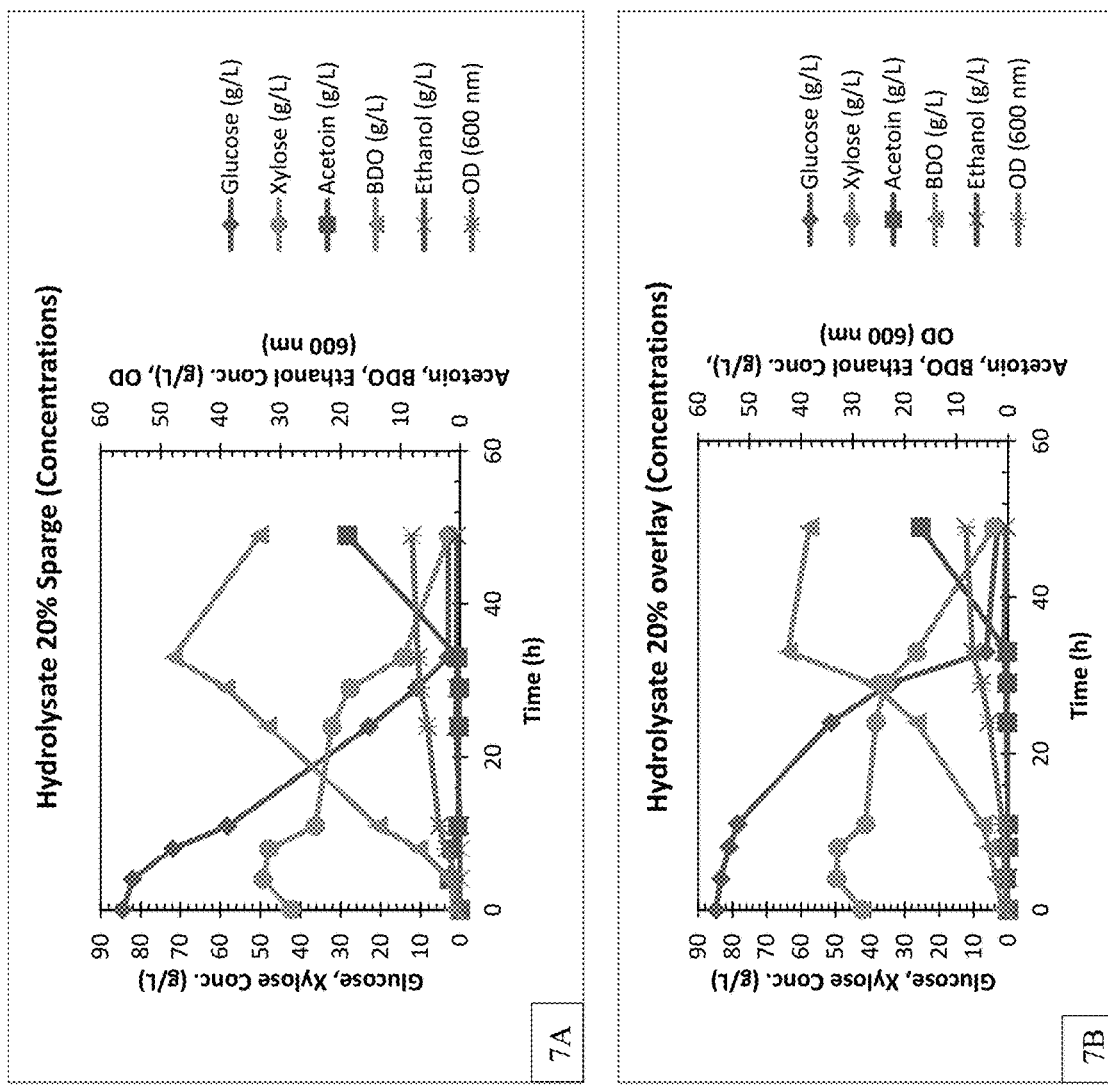
FIG. 7 depicts the fermentation profiles of the concentrations of glucose, xylose, acetoin, BDO, ethanol and the OD$_{600}$ a PDC knockout BDO producing *Z. mobilis* strain in DMR corn stover hydrolysate at 20% solid loadings.

The PDC knockout BDO producing Z. mobilis strain was subjected to further fermentation testing in a fermenter with pH control under limited oxygen conditions, initially using RMG medium. As shown in FIG. 5, the strain BC21 integrants 1 produced about 40 g/L of 2,3-BDO in less than 30 hours from about 10% glucose. The fermentation was further tested using DMR hydrolysate at 20% solid loadings supplied air either by sparging or overlay. As depicted in FIG. 7B, about 42 g/L of 2,3-BDO was produced under air overlay (200/300 ccm) from 20% solid loading DMR hydrolysate in which glucose were completely used and about 50% of xylose were used in 33 h. Xylose was completely used in 49 h; however, acetoin was mostly formed due to excessive air supplied during this period and partial conversion of 2,3-BDO was also observed. In the air sparging (100 ccm) condition, see FIG. 7A, the utilization both glucose and xylose in 20% solid loading DMR hydrolysate is faster as compared with air overlay, the strain produced 48 g/L 2,3-BDO from the corn stover hydrolysate. The high titers of 2,3-BDO from these fermentations using DMR corn stover hydrolysate exceeded the production of 35 g/L 2,3-BDO from glucose and xylose.

In another embodiment, 2,3-BDO produced by engineered Z. mobilis strains can be upgraded to butene, MEK and butadiene using aqueous catalytic processes resulting in significantly reduced separation costs. Further oligomerization of butene can produce long chain hydrocarbons used for gasoline, jet and diesel fuels having fuel production costs targeted at $2/GGE with coproduct.

Materials and Methods

Bacterial strain and growth conditions: Z. mobilis BC21 was revived from frozen glycerol stocks for about 6 to 8 h in 10 mL RMG2 (2% glucose, 10 g/L yeast extract, 2 g/L $KH_2PO_4$) with 50 µg/mL spectinomycin at 30° C. Strain BC21 is a derivative of Z. mobilis 9C (antibiotic resistance marker free) having a pBC21 plasmid (with BDO pathway genes—als, aldc and bdh). Strain 9C is an 8b derivative with both chloramphenicol and tetracycline antibiotics marker cured.

Figure 2:
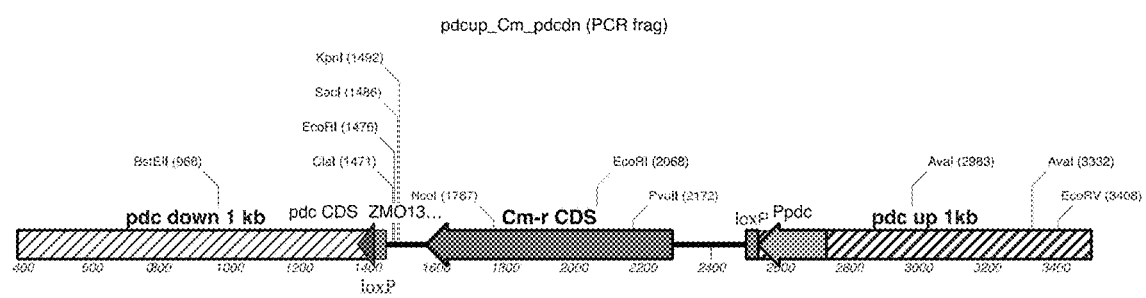
FIG. 2 depicts a pdc knockout construct in a fragment.

PDC gene knockout fragment construction: To knock out pdc by homologous recombination, a fragment (pdc_KO_Cm_loxP) containing upstream and downstream DNA to pdc gene and a chloramphenicol resistance gene (Cm) flanked by loxP was constructed, see FIG. 2. The fragment was also inserted into a suicidal vector as depicted in FIG. 1.

Electroporation transformation and 2,3-BDO strain selection: Z. mobilis or E. coli cells were transformed with plasmids by electroporation (Bio-Rad Gene Pulser, 0.1-cm gap cuvettes, 1.6 kV, 200 ohms, 25 µFD). Electro-competent Z. mobilis cells were prepared by centrifuging cells from cultures that had reached an optical density ($OD_{600}$)=0.4 to 0.6. The cell pellets were washed once in ice-cold sterile water, re-centrifuged, and washed again in 10% glycerol. These pellets were resuspended in 10% glycerol at a concentration approximately 1,000-fold higher than the starting culture. Competent cells were stored at −80° C. as small aliquots for later use. Transformants of E. coli or Z. mobilis were selected on LB or MMG agar plates, respectively, containing appropriate antibiotics. Due to the presence of a restriction/modification system, all plasmids were built in and isolated from a methylation-deficient E. coli strain, C2925 (New England Biolabs, MA), for successful transformations in Z. mobilis ATCC31821 derived hosts, BC21. DNA fragments prepared directly by PCR were used for electroporation.

The transformants grown on the selective spectinomycin (Sp) and chloramphenicol (Cm) antibiotics were further streaked on RMG plate with RMG Sp+Cm for single colony isolation, which were then used for colony PCR to confirm the introduction of plasmid and fragment with correct gene knockout using the primers of pdc genes to check the insert size. Colonies with expected PCR bands pattern were selected and inoculated into RMGSp200 for preservation and further flask evaluation.

Shake flask fermentation: Seed cultures of Z. mobilis strains harvested at exponential phase were inoculated into 125-mL shake flasks containing 40 mL media to a starting $OD_{600}$ of 0.1. The media were supplemented with spectinomycin (200 µg/mL) and Cm. Temperature was maintained at 30° C. with the shaking speed of 120 rpm or 180 rpm.

Fermentation: Fermentations to evaluate the strains for 2,3-BDO production were conducted in BioStat-Q plus fermenters with a 300 mL working volume, 300 rpm, a temperature of 30° C., and pH 5.8 controlled with KOH (4 N). The fermenters were inoculated from an overnight grown seed with initial OD of 0.1 @ 600 nm. Samples were taken at different time points for detail analysis.

Reviving: The strains were revived from a frozen state on RMG (5%) in 50 mL flat flask with 8 mL media and incubated overnight at 30° C. on a shaker incubator at 180 rpm. The grown, revived culture was used to start the seed for fermentation.

Seed preparation: The seeds were prepared in 125 mL baffled shake flask with 40 mL RMG (8%) using the grown revived culture with initial OD of 0.1 @600 nm. The seed flask was incubated at 30° C. overnight in shaking incubator with 180 rpm.

Hydrolysate: Hydrolysate used in this evaluation was DMR (A15). Hydrolysate was prepared from enzymatic saccharification of pretreated corn stover from mechanical disk refined processes.

Fermentations to evaluate the strains for BDO production were performed in BioStat-Q plus fermenters with a 300 mL working volume, 500 rpm, a temperature of 30° C., and pH 5.8 controlled with KOH (4 N). Fermentors were aerated by overlay or sparging from an air supply at a desired cubic centimeter per minute (ccm) flow rate and filtered through a 0.2 µl filter. The fermenters were inoculated from an overnight grown seed with initial OD of 0.1 @ 600 nm. Samples were taken at different time points for various analyses.

Fermentation data collection and analysis: Samples were taken at various time points and diluted for $OD_{600}$ measurements. In addition, samples were filtered through a 0.2 µm syringe filter into HPLC vials. Concentrations of glucose, xylose, 2,3-BDO, acetoin, xylitol, ethanol, HMF, furfural, lactic acid, glycerol, and acetic acid were determined from filtered sample supernatants by high performance liquid chromatography (HPLC) Agilent1100 series (Agilent, CA) utilizing a BioRad HPX-87H organic acids column and Cation Et guard cartridge (Bio-Rad, CA) operating at 55° C. A refractive index detector was used for the detection of various compounds. Dilute sulfuric acid (0.01 N) was used as the isocratic mobile phase at a flow rate of 0.6 mL min'. Sugar utilization, 2,3-BDO, acetoin, and ethanol titers and yield were calculated based on the HPLC data.

Figure 8:
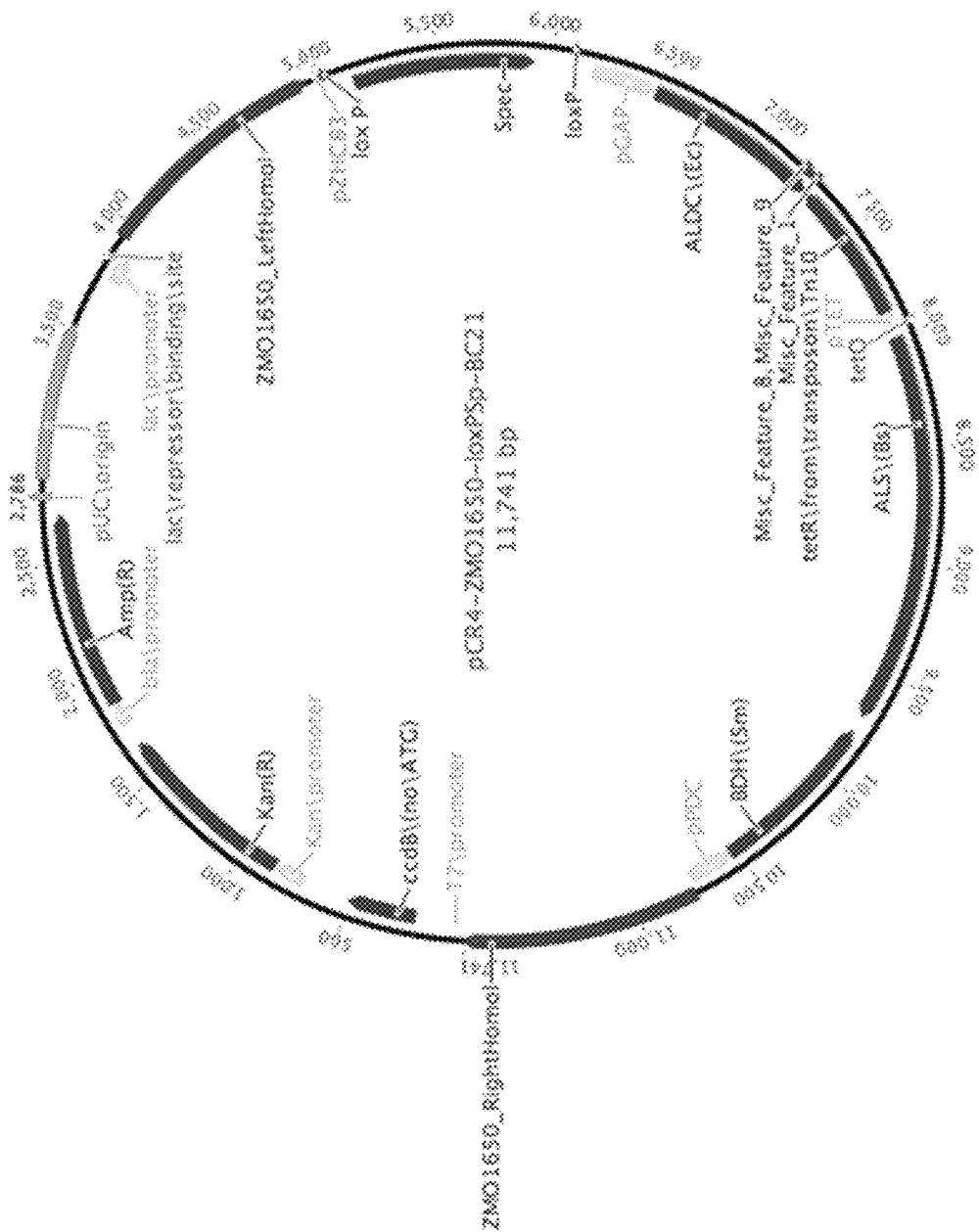
FIG. 8 depicts a plasmid map of pCR4-ZMO1650-loxPSp-BC21 which was used to integrate BDO production genes into *Z. mobilis* 9C.

Integration of Genes for the Production of 2,3-BDO into the Z. mobilis Chromosome The plasmid pCR4-ZMO1650-loxPSp-BC21, see FIG. 8, was used for integrating BDO genes into Z. mobilis 9C (a xylose utilizing Z. mobilis ZM4 strain free of antibiotic resistance) using homologous recombination by replacing ZMO1650 (ZMO_RS07410), a β-lactamase gene, with BDO genes from the BC21 plasmid. A spectinomycin marker flanked by loxP sites was used for the selection. The plasmid was created by Gibson assembly of the following PCR fragments, primers and respective annealing temperatures shown in Table 2 using primers listed in Table 3.

TABLE 2

PCR of fragments was prepared using NEB Q5 polymerase using the following primers, template sources and annealing temperatures.

| Template | PCR fragment | Size (kb) | Primers used | Annealing Temp |
|---|---|---|---|---|
| pCR4 TOPO | pCR4 TOPO vector backbone | 3.94 | oZH163 oZH172 | 66.2° C. |
| gDNA from ZM4 | 1 kb homology region left of ZMO1650 | 1.06 | oZH164 oZH175 | 60.5° C. |
| pMod2LoxP | loxP-Spec | 1.22 | oZH173 oZH174 | 66.0° C. |
| pBC21 | BDO genes | 4.6 | oZH176 oZH169 | 61.2° C. |
| gDNA from ZM4 | 1 kb homology region right of ZMO1650 | 1.02 | oZH170 oZH171 | 67.9° C. |

TABLE 3

Primers used for Table 2 PCR experiments.

| Primer | Sequence of Primer |
|---|---|
| oZH163 (SEQ ID NO: 1) | CGTTTAAACCTGCAGGACTAGTC |
| oZH164 (SEQ ID NO: 2) | gggactagtcctgcaggtttaaa cgATTGAGGTCATTGCATCTGAT ATTC |
| oZH169 (SEQ ID NO: 3) | agaccgcaccttaTACTAGATAT CGCTCATGATCG |
| oZH170 (SEQ ID NO: 4) | gcgatatctagtaTAAGGTGCGG TCTTGATTAGCC |

TABLE 3-continued

Primers used for Table 2 PCR experiments.

| Primer | Sequence of Primer |
|---|---|
| oZH171 (SEQ ID NO: 5) | gaattgaatttagcggccgcgaa ttGATGATGTCGCCGCCTTGGA |
| oZH172 (SEQ ID NO: 6) | AATTCGCGGCCGCTAAATTC |
| oZH173 (SEQ ID NO: 7) | tttataagaataTTGTTGGCTAG TGCGTAGTC |
| oZH174 (SEQ ID NO: 8) | gggttgttgatcgaacCGGGGAT CCTCTAGAGTCGA |
| oZH175 (SEQ ID NO: 9) | CACTAGCCAACAATATTCTTAAG AAAGAATTCTTTTGTTCTTTC |
| oZH176 (SEQ ID NO: 10) | TAGAGGATCCCCGGTTCGATCAA CAACCCGAATC |

After assembly, the plasmid was electroporated into electrocompetent C2925 from NEB (dam-dcm-). The plasmid was verified by restriction mapping and the sequence confirmed and subsequently integrated into Z. mobilis 9C and plated both on MMGSp (mating medium with 5% glucose and 200 µg/mL spectinomycin) under both aerobic and anaerobic (in anaerobic chamber with CO2 pack) conditions. Only colonies plated under aerobic conditions were positive for BDO gene integration, the vector backbone was integrated via a single crossover recombination. Isolates were serially transferred 9 times in the presence of RMGSp200 @ 30° C. in test tubes shaken at 120 rpm to allow for the 2nd crossover event eliminating the vector backbone before isolating further on RMGSp200 plates. The strain was consequently designated ZHC129. In order to cure the strain of spectinomycin resistance, the strain was transformed with the plasmid expressing the Cre recombinase. Following serial transfers, the spectinomycin marker was removed and the plasmid cured resulting in strain ZHC133. Knockout of the pdc gene of ZHC133 was achieved using the above described procedures and resulted in the strain BC42C.

Figure 9:
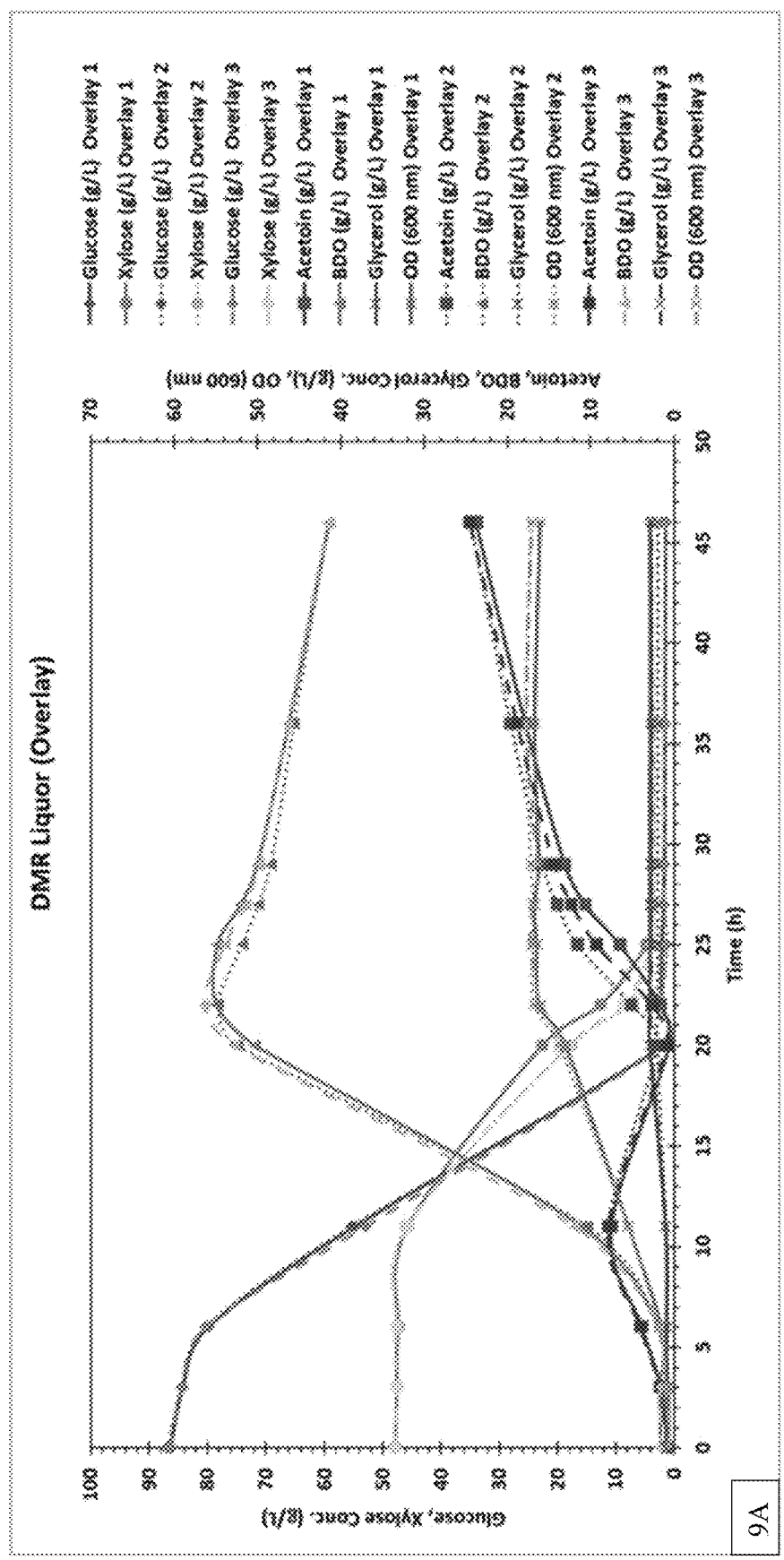
FIG. 9 depicts the fermentation profiles of the concentrations of glucose, xylose, acetoin, glycerol, BDO, and the $OD_{600}$ using a deacetylation and mechanical refining (DMR) process for treating the corn stover.
Figure 9:
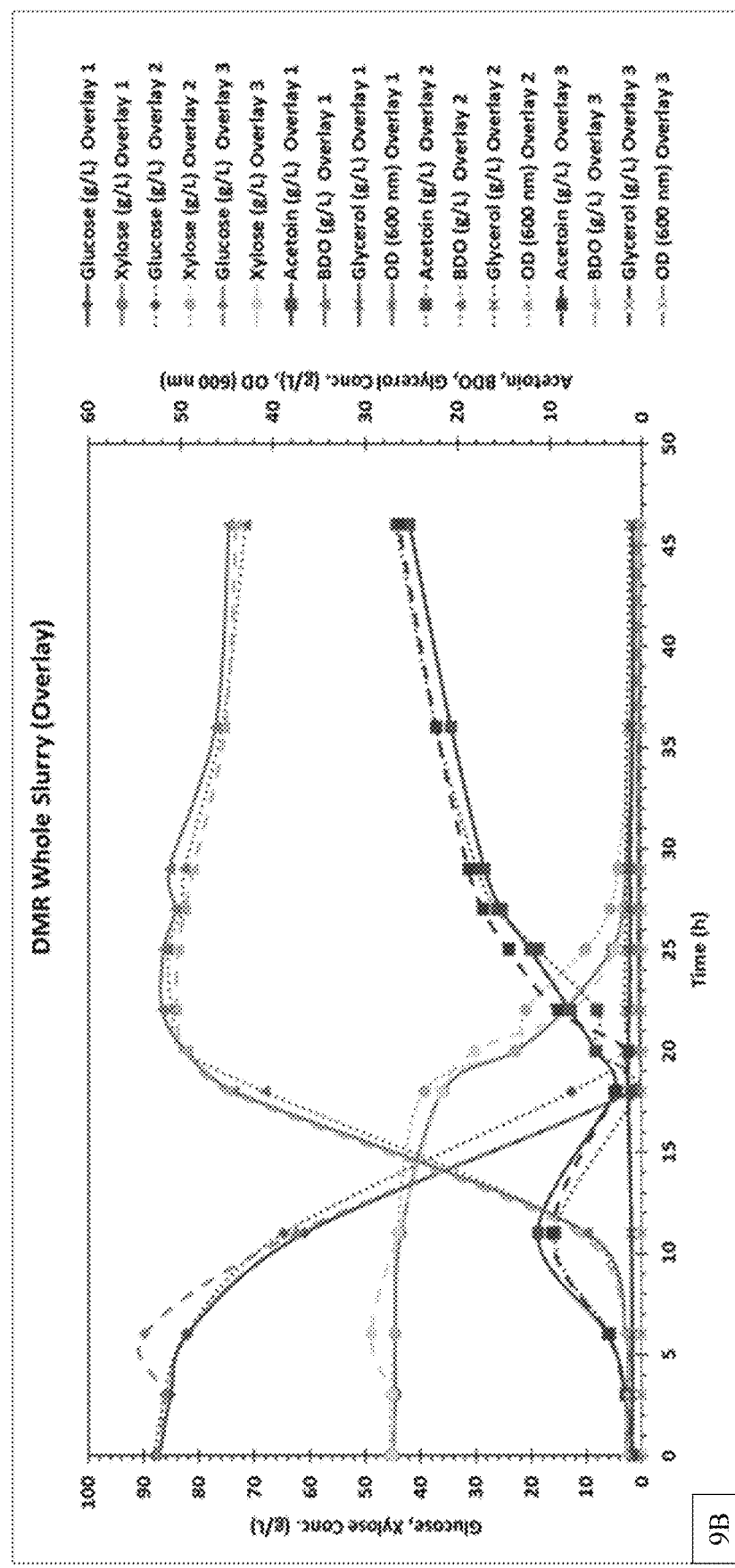

FIG. 9 depicts using hydrolysate liquor vs whole slurry (without separation of biomass solids) for fermentation experiments using BC21 integrant 1 strain BC42C. The concentrations of fermentation metabolites and $OD_{600}$ as depicted in FIG. 9A under batch conditions that used DMR liquor from 20% solids. The fermentation medium of experiments that resulted in the data depicted in FIG. 9A had starting concentrations of sugars of glucose at 86 g/L and xylose at 48 g/L. As depicted in FIG. 9A, the maximum concentration of BDO was 54 g/L with 9 g/L acetoin, and the final BDO concentration was at 41 g/L with 24 g/L acetoin.

For experiments, the results of which are depicted in FIG. 9B, the conditions used DMR 20% solids (also referred to as whole slurry conditions), the fermentation media were grown under batch conditions using DMR 20% solids (whole slurry) with BC21 integrant 1 strain BC42C and had starting sugars concentrations of glucose at 87 g/L and xylose at 45 g/L. As depicted in FIG. 9B, the maximum concentration of BDO was at 51 g/L with 12 g/L acetoin with the final BDO concentration being at 43 g/L with 26 g/L acetoin.

Figure 10:
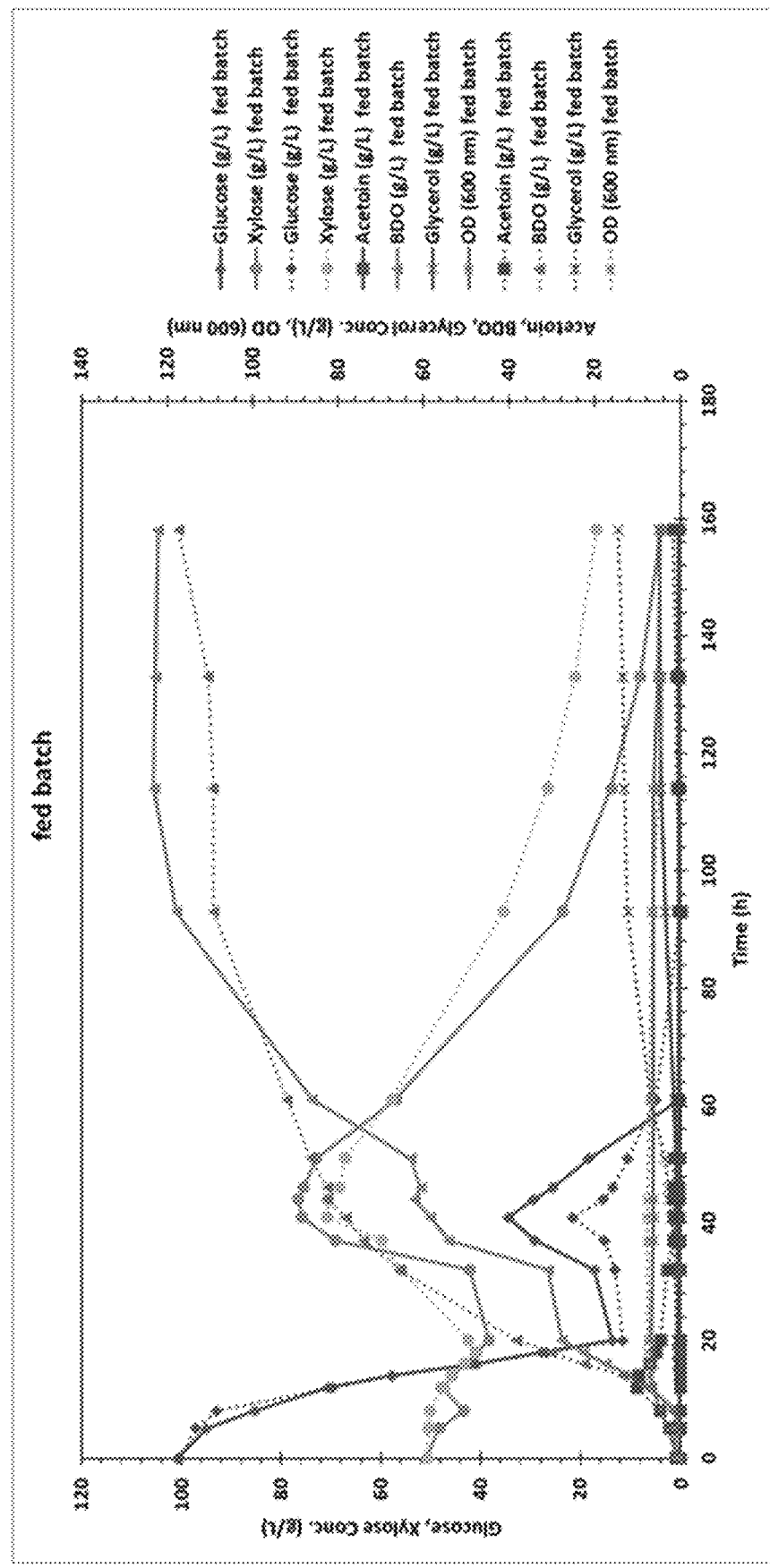
FIG. 10 depicts the fermentation profiles of the concentrations of glucose, xylose, acetoin, glycerol, BDO, and the $OD_{600}$ using a fed batch fermentation of BC21 integrants 1 containing glucose and xylose that resulted in BDO titers of about 120 g/L.

For the results of fermentation experiments using strain BC42C under batch fed conditions as depicted in FIG. 10, the concentrations used in the media were RMGX (103:52

(the ration of glucose to xylose)) with spectinomycin grown at 30° C., pH 5.8, pH controlled with 4N KOH, and shaken at 700 rpm. The engineered cells were batch fed with 650 g/L feed with a total of 100 mL added at a rate of 4.2 mL/hr with shaking at 350 rpm. As depicted in FIG. 10, the final titer of BDO was at about 120 g/L with about 1 g/L acetoin and about 14 g/L glycerol.

Figure 11:
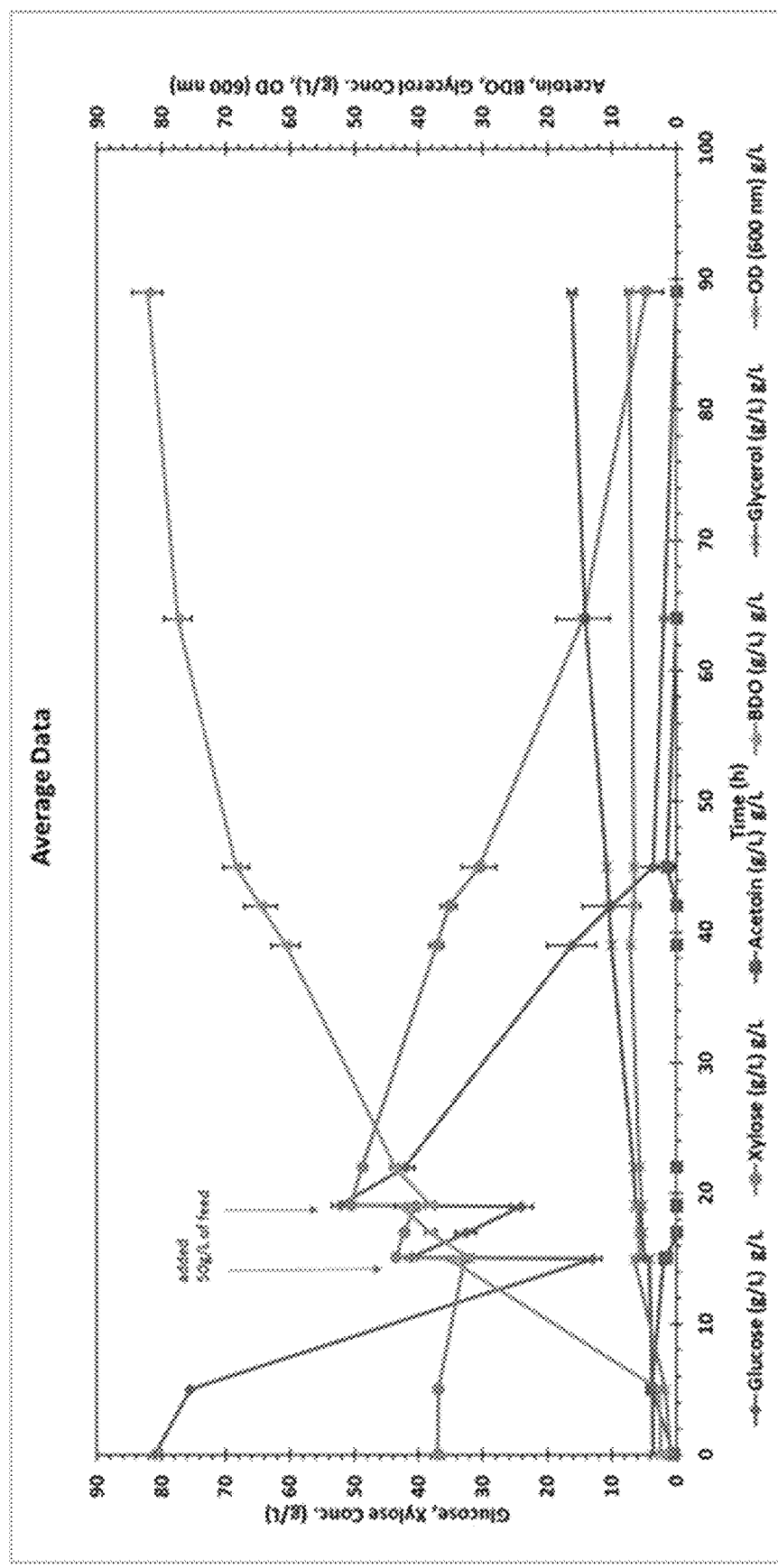
FIG. 11 depicts the average of the hydrolysate liquor profiles of the concentrations of glucose, xylose, acetoin, glycerol, BDO, and the $OD_{600}$ for three fed-batch fermentations resulting in up to 84 g/L BDO by using hydrolysate liquor containing glucose and xylose.

FIG. 11 depicts the average of the hydrolysate liquor profiles of the concentrations of glucose, xylose, acetoin, glycerol, BDO, and the $OD_{600}$ for three fed-batch fermentations of strain BC42C resulting in up to 84 g/L BDO by using hydrolysate liquor containing glucose and xylose. The data depicted in FIG. 11 is displayed in tabular form in Table 4.

TABLE 4

Measurements of fermentation metabolites and BDO as depicted in FIG. 11.

| Fermenter | OD 600 nm | Glucose g/L | Xylose g/L | BDO g/L | Glycerol g/L | Sugars consumed % | BDO yield (gS/gP) | Productivity (g/L/h) |
|---|---|---|---|---|---|---|---|---|
| 1 | 7.71 | 0.00 | 2.43 | 84.70 | 16.09 | 98.72 | 0.43 | 0.991 |
| 2 | 7.54 | 0.00 | 7.58 | 79.98 | 16.94 | 95.92 | 0.42 | 0.929 |
| 3 | 6.96 | 0.00 | 3.98 | 82.04 | 15.06 | 97.76 | 0.45 | 0.959 |

The effects of various aeration and agitation conditions in RMG (rich medium with glucose) 10% with spectinomycin using the genome integrated strain BC42C are shown in Table 5.

TABLE 5

Growth conditions and concentrations of fermentation metabolites using genome integrated strain BC42C.

| Fermenter Conditions | | Sparging | | | | | Overlay | | | |
|---|---|---|---|---|---|---|---|---|---|---|
| RPM | CCM | BDO (g/L) | Acetoin (g/L) | Productivity (g/L/h) | Yield (gS/gP) | Time (h) | BDO (g/L) | Acetoin (g/L) | Productivity (g/L/h) | Yield (gS/gP) | Time (h) |
| 300 | 40  | 38.17 | 0.04  | 0.76 | 0.44 | 50 | 46.18 | 0.68 | 0.69 | 0.43 | 67 |
| 300 | 100 | 45.72 | 1.30  | 0.91 | 0.44 | 50 | 45.68 | 0.17 | 0.68 | 0.43 | 67 |
| 300 | 160 | 44.83 | 0.16  | 1.12 | 0.43 | 40 | 46.14 | 0.15 | 0.63 | 0.47 | 73 |
| 500 | 40  | 29.97 | 19.86 | 0.62 | 0.28 | 48 | 36.98 | 8.45 | 1.03 | 0.37 | 39 |
| 500 | 100 | 45.86 | 0.12  | 2.18 | 0.46 | 21 | 40.67 | 5.14 | 1.13 | 0.41 | 39 |
| 500 | 100 | 45.70 | 0.09  | 1.90 | 0.45 | 24 | 44.51 | 0.84 | 1.08 | 0.43 | 43 |
| 500 | 100 | 46.33 | 3.21  | 1.72 | 0.42 | 27 | 40.11 | 0.14 | 1.25 | 0.44 | 32 |
| 500 | 160 | 45.97 | 0.46  | 1.92 | 0.45 | 24 | 46.96 | 0.12 | 1.47 | 0.44 | 32 |
| 700 | 40  | 33.22 | 8.89  | 1.70 | 0.32 | 20 | 41.91 | 0.35 | 1.69 | 0.45 | 26 |
| 700 | 100 | 17.08 | 16.73 | 0.95 | 0.17 | 18 | 44.54 | 1.52 | 1.81 | 0.45 | 26 |
| 700 | 160 | 9.55  | 43.53 | 0.20 | 0.09 | 48 | 38.62 | 7.36 | 1.61 | 0.40 | 26 |

The foregoing disclosure has been set forth merely to illustrate the invention and is not intended to be limiting. Since modifications of the disclosed embodiments incorporating the spirit and substance of the invention may occur to persons skilled in the art, the invention should be construed to include everything within the scope of the appended claims and equivalents thereof.

Other objects, advantages, and novel features of the present invention will become apparent from the following detailed description of the invention when considered in conjunction with the accompanying drawings.

What is claimed is:

1. A non-naturally occurring *Zymomonas mobilis* that does not produce ethanol, lacks a functional pyruvate decarboxylase gene, lacks antibiotic markers and that produces 2,3-butanediol through using the gene products of operably connected exogenous genes acetolactate synthase (ALS), acetolactate decarboxylase (ALDC), and butanediol dehydrogenase (BDH) wherein the exogenous genes are integrated into the chromosomal location of a pyruvate decarboxylase gene of the *Zymomonas mobilis*; and wherein the integration of the exogenous genes eliminates the native chromosomal gene for pyruvate decarboxylase; and wherein the *Zymomonas mobilis* produces 2,3-butanediol in a growth medium that lacks antibiotics; and wherein the 2,3-butanediol produced is at least 96% of the theoretical yield from a carbon source for the production of the 2,3-butanediol; and wherein the 2,3-butanediol is produced up to a concentration of about 120 g/L.

2. The non-naturally occurring *Zymomonas mobilis* of claim 1 that produces 2,3-butanediol for at least 150 hours.

3. The non-naturally occurring *Zymomonas mobilis* of claim 1 that produces 2,3-butanediol at about 2.18 g/L/h.

4. The non-naturally occurring *Zymomonas* species of claim 1 wherein the exogenous genes are endogenous to organisms selected from the group consisting of *Bacillus subtilis*, *Enterobacter cloacae* and *Serratia marcescens*.

5. A method for making 2,3-butanediol using the *Zymomonas* of claim 1 wherein the method comprises the step of contacting the *Zymomonas* with at least one sugar selected from the group consisting of glucose and xylose as a carbon source for the production of 2,3-butanediol.

* * * * *

SEQUENCE LISTING

<160> NUMBER OF SEQ ID NOS: 10

<210> SEQ ID NO 1
<211> LENGTH: 23
<212> TYPE: DNA
<213> ORGANISM: Artificial Sequence
<220> FEATURE:
<223> OTHER INFORMATION: Primer ZH163

```
<400> SEQUENCE: 1
cgtttaaacc tgcaggacta gtc                                           23

<210> SEQ ID NO 2
<211> LENGTH: 50
<212> TYPE: DNA
<213> ORGANISM: Artificial Sequence
<220> FEATURE:
<223> OTHER INFORMATION: Primer ZH164

<400> SEQUENCE: 2
gggactagtc ctgcaggttt aaacgattga ggtcattgca tctgatattc              50

<210> SEQ ID NO 3
<211> LENGTH: 35
<212> TYPE: DNA
<213> ORGANISM: Artificial Sequence
<220> FEATURE:
<223> OTHER INFORMATION: Primer ZH169

<400> SEQUENCE: 3
agaccgcacc ttatactaga tatcgctcat gatcg                              35

<210> SEQ ID NO 4
<211> LENGTH: 35
<212> TYPE: DNA
<213> ORGANISM: Artificial Sequence
<220> FEATURE:
<223> OTHER INFORMATION: Primer ZH170

<400> SEQUENCE: 4
gcgatatcta gtataaggtg cggtcttgat tagcc                              35

<210> SEQ ID NO 5
<211> LENGTH: 45
<212> TYPE: DNA
<213> ORGANISM: Artificial Sequence
<220> FEATURE:
<223> OTHER INFORMATION: Primer ZH171

<400> SEQUENCE: 5
gaattgaatt tagcggccgc gaattgatga tgtcgccgcc ttgga                   45

<210> SEQ ID NO 6
<211> LENGTH: 20
<212> TYPE: DNA
<213> ORGANISM: Artificial Sequence
<220> FEATURE:
<223> OTHER INFORMATION: Primer ZH172

<400> SEQUENCE: 6
aattcgcggc cgctaaattc                                               20

<210> SEQ ID NO 7
<211> LENGTH: 33
<212> TYPE: DNA
<213> ORGANISM: Artificial Sequence
<220> FEATURE:
<223> OTHER INFORMATION: Primer ZH173

<400> SEQUENCE: 7
tttcttaaga atattgttgg ctagtgcgta gtc                                33

<210> SEQ ID NO 8
<211> LENGTH: 36
```

```
<212> TYPE: DNA
<213> ORGANISM: Artificial Sequence
<220> FEATURE:
<223> OTHER INFORMATION: Primer ZH174

<400> SEQUENCE: 8
gggttgttga tcgaaccggg gatcctctag agtcga                           36

<210> SEQ ID NO 9
<211> LENGTH: 44
<212> TYPE: DNA
<213> ORGANISM: Artificial Sequence
<220> FEATURE:
<223> OTHER INFORMATION: Primer ZH175

<400> SEQUENCE: 9
cactagccaa caatattctt aagaaagaat tcttttgttc tttc                  44

<210> SEQ ID NO 10
<211> LENGTH: 34
<212> TYPE: DNA
<213> ORGANISM: Artificial Sequence
<220> FEATURE:
<223> OTHER INFORMATION: Primer ZH176

<400> SEQUENCE: 10
tagaggatcc ccggttcgat caacaacccg aatc                             34
```